United States Patent

Rowe

[11] Patent Number: 5,985,891
[45] Date of Patent: Nov. 16, 1999

[54] PREVENTION OF ADVERSE BEHAVIOR, DIARRHEA, SKIN DISORDERS AND INFECTIONS OF THE HIND GUT ASSOCIATED WITH ACIDIC CONDITIONS IN HUMANS AND ANIMALS BY THE APPLICATION OF ANTIBIOTICS

[76] Inventor: James Baber Rowe, 411 Rockvale Road, Armidale, New South Wales 2350, Australia

[21] Appl. No.: 08/860,562
[22] PCT Filed: Dec. 29, 1995
[86] PCT No.: PCT/AU95/00884
 § 371 Date: Aug. 29, 1997
 § 102(e) Date: Aug. 29, 1997
[87] PCT Pub. No.: WO96/20709
 PCT Pub. Date: Jul. 11, 1996

[30] Foreign Application Priority Data

Dec. 29, 1994 [AU] Australia ............................. PN 0338

[51] Int. Cl.$^6$ .................................................. A61K 31/445
[52] U.S. Cl. ........................................... 514/293; 514/375
[58] Field of Search ..................................... 514/293, 375

[56] References Cited

U.S. PATENT DOCUMENTS 3,574,819 4/1971 Gross et al. .
5,436,003 7/1995 Rohde, Jr. et al. .

FOREIGN PATENT DOCUMENTS

32284/89 10/1989 Australia .
203586 12/1986 European Pat. Off. .
89/01970 3/1989 WIPO .

OTHER PUBLICATIONS

Nagaraja et al; J Anim Sci, 53(1) 205–216, 1981.
Muir et al, J Anim Sci, 50(3), 547–553, 1981.
Merck Manual, pp. 788–813, 1987.
Merck Index, 10 ed, #8374, p. 1225, 1983.
WPIDS, Rowe AN 89–287158, 1989.
WPIDS, Bock et al, AN 92–408921, 1992.
HCAPIUS, 120: 162407, Godfrey et al, 1993.

Primary Examiner—Rebecca Cook
Attorney, Agent, or Firm—Lowe Hauptman Gopstein Gilman & Berner

[57] ABSTRACT

A method of treating adverse behavior in animals, manifested in secondary effects such as, in horses, excitability, difficult handling, coprophagy, wood chewing and grasping, or wind sucking, by controlling the formation and accumulation of acid in the hind gut (large intestine) of the gastrointestinal tract that results from the fermentation of excess carbohydrates in the hind gut. This is accomplished by ingesting certain antibiotics with or without combination thereof with certain enzymes. Of specific merit in this invention is the use of virginiamycin to control the passage of carbohydrates into the gastrointestinal tract and the fermentation of these carbohydrates therein. This controls, the accumulation of acid in the digestive tract.

23 Claims, 6 Drawing Sheets

PREVENTION OF ADVERSE BEHAVIOR, DIARRHEA, SKIN DISORDERS AND INFECTIONS OF THE HIND GUT ASSOCIATED WITH ACIDIC CONDITIONS IN HUMANS AND ANIMALS BY THE APPLICATION OF ANTIBIOTICS

This is a 371 of PCT/AU95/00884 filed Feb. 29, 1995.

TECHNICAL FIELD

This invention relates to the treatment or prophylaxis of conditions resulting from the accumulation of acid in the gastrointestinal tract of a human or an animal, said accumulation resulting from the fermentation of carbohydrate in the gastrointestinal tract of the human or animal. The problems associated with fermentation in the gastrointestinal tract, and overcome with treatment, include adverse behaviour, diarrhoea, skin disorders and infections of the hind gut associated with acidic conditions.

BACKGROUND ART

The digestive processes in humans and in monogastric animals such as pigs, birds and horses, involves acid digestion in the stomach followed by absorption of simple sugars, amino acids, fats etc from the small intestine. The undigested material then passes into the large intestine which contains a dense population of bacteria and where fermentation of fibrous material and undigested sugars, starches and carbohydrates occurs. Ruminants such as sheep and cattle, related animals and some kangaroo species have a forestomach in which feed is fermented prior to acid digestion. These animals also have a hind gut where fermentative digestion also occurs.

The hind gut (or large intestine) varies in size and structure depending on the nature of the diet and the extent of fibre digestion which normally occurs. In humans and animals it consists of a colon and caecum and both of these compartments can vary in their size and in their complexity of structure. Normal fermentation results in the production of volatile fatty acids (VFA) which are absorbed from the gut. In the hind gut the pH is maintained, under normal conditions within the range 6 to 7.5, as it is within this range that bacterial fermentation is most efficient. If starch, sugar or other carbohydrate enters the hind gut it is rapidly fermented, and this rapid fermentation can lead to the accumulation of lactic acid, which is a stronger acid than the VFA and it is not absorbed as quickly. The accumulation of lactic acid leads to a decline in pH. These acidic conditions can result in damage to and death of bacteria with the release of endotoxins. The low pH can also initiate the release of various peptide hormones and/or enzymes by the gut wall and these molecules can be active in different parts of the body. The endotoxins and/or hormones and/or other chances which result from high levels of hind gut fermentative activity may affect numerous functions of the body. There is therefore a wide range of biological consequences which result from an acidic pattern of fermentation in the hind gut.

Consequently, there are several adverse effects which excessive levels of starch and/or sugar can have on humans and animals. These include behavioural changes in horses and humans, diarrhoea in animals and humans, skin disorders in humans and infections of the hind gut associated with acidic conditions. It is also known that severe carbohydrate overload in animals can cause significantly reduced intake and in some instances, death. Under extreme models of carbohydrate overload in which non-physiological amounts of glucose and/or starch are administered to animals, acidic patterns of fermentation develop, leading to conditions such as diarrhoea in ruminants. Under normal nutritional circumstances isolated episodes of diarrhoea are not considered to be a result of incomplete carbohydrate absorption in the small intestine and the occurrence of excessive fermentation in the hind gut. It has generally been considered to be a fact in human and animal digestive physiology, that starches and sugars are completely digested and absorbed from the digestive tract prior to the hind gut. Because complete digestion and absorption has been assumed, the occurrence of hind gut fermentative acidosis has never been considered as a potential health problem under normal dietary conditions. Therefore, it has never been recognised as the possible primary cause of abnormalities such as behavioural changes, diarrhoea and skin disorders linked to the inclusion of starches and sugars in the diet. Consequently the treatment of the conditions such as behavioural changes, the control of diarrhoea, prevention of skin diseases and infections of the hind gut associated with acidic conditions, through treatments to control acid accumulation in the hind gut, are not known in any species under normal conditions.

The link between the inclusion of carbohydrate such as starch and sugars in the diet of horses and humans and subsequent adverse behaviour is known. The mechanism by which the carbohydrate source in the diet effects behaviour has not been understood and in the past treatment has relied totally on avoidance. Horses fed high levels of grain become excitable, difficult to handle and they develop a range of behavioural characteristics such as coprophagy, wood chewing and grasping or wind sucking. These behavioural abnormalities are currently overcome or reversed by reducing the amount of cereal grain in the diet or completely removing the source of starch or carbohydrate. This is the normal practice when the behavioural problems become severe. There has hitherto been no other known way of treating this condition. Similarly, in humans, a proportion of children are known to become hyperactive when they consume certain foods rich in sugars and/or processed starch. The consumption of these feeds is also thought to be associated with the condition "attention deficit disorder". Hitherto, the only known treatment for these behavioural changes has been avoidance of processed starches and sugars. In intensively housed pigs fed diets containing high levels of cereal grain, the problem of tail biting and other patterns of "bored" behaviour have been recognised and treated by providing a range of alternative activities for the pigs, such as balls, ropes and chains for them to push and play with.

There are numerous causes of diarrhoea. Diarrhoea is a result of excessive secretion of fluids into the gut and/or a failure to absorb sufficient fluid from the gastro-intestinal tract. Fluid loss into the gut can occur through changes in gut permeability, through increased osmotic concentration in the gut or through abnormal intestinal motility. The permeability can be affected by any factors which produce inflammation and increased capillary permeability. It can also be increased by raised venous pressure or any factor which disrupts the tight packing of the epithelial cells in the hind gut. Osmotic diarrhoea can result from the inclusion of non-absorbable solutes in the diet or through the production of osmotically active molecules within the gut. The osmotic pressure can be increased either by microbial breakdown of large particles to smaller particles and through the enzymatic conversion of large molecules such as starch to a greater number of small molecules such as volatile fatty acids and lactic acid. The process of rapid fermentation of starches and sugars can lead to a sudden increase in osmotically active molecules and diarrhoea.

Intestinal motility may increase the incidence of diarrhoea through increased rate of gastric emptying, increased small bowel transit and increased rate of passage through the hind gut. These processes result in more secretion into the gut and reduced absorption of solutes and this leads to diarrhoea. The specific causes of abnormal gut motility are largely unknown. Conditions such as irritable colon syndrome or irritable bowel disease are thought to be associated with abnormal gut motility. There is no known treatment for these conditions.

The mechanism by which viral agents cause diarrhoea is not known. Infection with transmissible gastro-enteritis virus, or human rotavirus are known to reduce the absorptive efficiency of the gastro-intestinal tract. There does not appear to be evidence that they increase secretion into the gut. There is no known treatment against viral diarrhoea.

Fluid loss into the gut by active mechanisms occurs in response to a variety of bacterial exotoxins. These exotoxin or enterotoxins are thought to promote active secretion of electrolytes and water through activation of the enzyme adenyl cyclase. Examples of bacteria known to promote diarrhoea include *Vibrio cholerae*, enterotoxicogenic *Escherichia coil, Shigella dysenteriae, Bacillus cereus, Clostridium perfringens, Salmonella enteriditis* and *Klebsiella pneumoniae*. Diarrhoea of toxic microbial origin is thought to be the most common type of diarrhoea. This form of diarrhoea is commonly created by vaccination in the case of cholera and/or through antibiotic treatment for these and other microbial pathogens. It is therefore well known to treat diarrhoea with antibiotic agents specifically effective against pathogenic bacteria in the gut. Broad spectrum antibiotics such as co-trimoxazol, erythromycin, penicillins, cephalosporins etc are used in these situations at therapeutic concentrations to clear the gut of pathogenic organisms. This type of diarrhoea caused by active fluid loss through the effect of pathogenic bacteria via the enzyme adenyl cyclase is completely different to the osmotic diarrhoea caused by accumulation of osmotically active particles and molecules in the intestine. While diarrhoea associated with the active secretion resulting from toxic bacteria has been commonly treated using antibiotics there has hitherto been no treatment available for osmotic diarrhoea other than avoidance of feeds and substrates known to cause the problem. It is this form of diarrhoea that is the object of the invention.

The blue green algae *Microcystis aeruginosa* is widely distributed in water sources and is also known to produce a toxin responsible for initiating diarrhoea. The only known treatment for this is avoidance of polluted water.

Diarrhoea can also be caused by abnormal endocrine function which produces abnormally high levels of secretion or which inhibits normal intestinal absorption. These hormonal abnormalities are poorly understood and there are no known methods of treating these abnormalities.

There are numerous recorded examples of skin conditions such as psoriasis which respond to changes in the amount and type of carbohydrate consumed. There are also many well documented cases where the practice of food combining has reduced the incidence of skin disorders such as psoriasis. The practice of food combining is designed to maximise the efficiency with which starches and sugars are absorbed from the small intestine. While the link between certain types of starch in the diet and skin disorders is well known the mechanism by which starches and sugar in the diet affect these skin abnormalities is not understood. Hitherto, the only existing treatment for these skin conditions is therefore avoidance of foods known to cause the problem and the use of topical application of steroidal creams to control the symptoms.

The hind gut disease, swine dysentry, is caused by pathogenic bacteria *Serpulina* (previously Treponema) *hysdysenteriae*. It has been shown that infection with *S. hyodysenteriae* can be prevented by feeding boiled rice instead of wheat-based diets. Hitherto, the control of this disease through preventing acidic conditions in the hind gut is not known. Acidity in the hind gut predisposes it to infection by bacteria and other pathogens which tolerate acidic conditions. The control of these pathogens by maintaining normal pH in the hind gut is not known.

Accordingly there is a need for improved treatment or prophylaxis of conditions resulting from the accumulation of acid in the gastrointestinal tract of a human or an animal, said accumulation resulting from fermentation of carbohydrate in the gastrointestinal tract of the human or animal.

OBJECTION OF THE INVENTION

An object of the invention is to modify human and animal behaviour, the incidence of diarrhoea to provide a method for the prophylaxis and treatment of skin disorders and the prevention of infection of the hindgut through controlling the pattern of fermentation in the digestive tract through preventing lactic acid accumulation and low pH. These chances in the gut may affect behaviour and skin disorders directly through lactic acid absorbed into the blood, through low gut pH reducing systemic acid:base balance, and/or indirectly through endotoxins hormones and/or combinations of these effects.

DISCLOSURE OF THE INVENTION

The method of the present invention for controlling hind cut fermentative acidosis is through the use of antibiotic type compounds such as virginiamycin, which are specifically active against the gram positive bacteria responsible for the production of lactic acid under conditions of low pH. This proposed use of antibiotics is completely different to the known use of antibiotics to treat diarrhoea. The traditional use of antibiotics aims to eliminate the pathogenic bacteria in the gut (normally the small intestine) which produce enterotoxins which actively stimulate secretion into the gut and cause diarrhoea. The antibiotic use of the present invention aims to control the population of gram positive bacteria which produce lactic acid within the gut and modify their biochemical pathways to produce a safe pattern of fermentation. The treatment does not seek to totally eliminate gram positive bacteria from the hind gut and would be ineffective against the pathogenic bacteria which produce classic secretory diarrhoea. The proposed treatment targets different bacterial species, in a different part of the digestive tract, using a different types of antibiotics than is the case with the treatment of classic forms of secretory diarrhoea resulting from the presence of pathogenic bacteria in the intestine. For example the antibiotic virginiamycin it is not absorbed from the gastrointestinal tract and therefore has no systemic anti-microbial activity.

An alternative method of preventing the development of hind gut fermentative acidosis is through the use of enzymes active in the breakdown of non-starch polysaccharides such as arabinoxylans and glucans which increase viscosity of digesta and prevent the normal digestion of starch and other carbohydrates. Enzymes can also be used to make the digestion of starch and/or the breakdown of disaccharides and oligosaccharides to monosaccharides more rapid and more complete and this results in reduced passage of fermentable carbohydrate to the hind gut. The use of such exogenous enzymes to improve the digestion of starch, and other forms of readily fermentable carbohydrate, reduces the amount of substrate which would otherwise pass into the hind gut as substrate for rapid fermentation and the formation of acid. Enzymes active in the breakdown of non-starch polysaccharides and the bonds which form between proteins and starches are used in monogastric nutrition in order to increase the overall digestibility of the diet and to reduce viscosity of the digesta in the small intestine but have not been used as a method for improving behaviour, overcoming diarrhoea, treating skin disorders in humans and for controlling infections of the hind gut associated with acidic conditions. The use of enzymes to enhance the rate and extent of starch and disaccharide breakdown and digestion is not practiced as it is assumed that these substances are rapidly and completely digested. The importance of preventing these substrates from being fermented in the hind gut to produce acidic conditions has not been recognised and is the subject of this invention.

A further way of preventing hind gut acidosis is to use clays such as bentonite, montmorrilonite, zeolite or kaolinite which may act in the hind gut in a number of ways. By adsorbing ions they reduce the osmolarity of digesta and therefore reduce some of the adverse effects associated with osmotic diarrhoea. This is one of the ways in which kaolinite clays may act as a component of mixtures used to reduce diarrhoea. Clays such as bentonite added to ruminant diets slow fermentation and reduce the total digestibility of the diet. Evidence for this is provided by the fact that the inclusion of bentonite reduced the total concentration of volatile fatty acids from 125 mmol/L to around 90 mmol/L in sheep fed grain supplements, maintained a higher pH (6.2 compared to 5.9) and reduced apparent organic matter digestibility from 71.5 to 66.6% (E. Aitchison. J. Rowe and G. Rix 1986, Proc Nutr Soc Aust 11, 111–114). By slowing fermentation, clays may reduce the extent of acid accumulation in the gastrointestinal tract during bacterial break down of carbohydrates. Clays have their biological and chemical effects through the multiple binding sites for charged particles and the mechanism by which different types of clay affect fermentation are therefore likely to be similar.

In the development of this discovery animal models have been used. The anatomy and digestive physiology of dogs and pigs is similar to humans. Even in the horse, which has an enlarged hind gut many of the principles are common. The similarities are particularly pertinent in the case of fermentative digestion in the hind gut where the bacterial species are likely to be common since the organisms occur ubiquitously and respond to the availability of substrate, temperature and pH in a similar way wherever they grow. It is therefore reasonable to extrapolate from the findings in animals to predict efficacy in humans. Experimentation with human subjects is not justified during early development of a discovery such as this.

According to a first embodiment of this invention there is provided a method for the treatment or prophylaxis of adverse behaviour diarrhoea a skin disorder or an infection of the hind gut resulting from the accumulation of acid in the gastrointestinal tract of a human or an animal said accumulation resulting from the fermentation of carbohydrate in the gastrointestinal tract of said human or animal, which method comprises administering to said human or animal an effective amount of an agent capable of preventing or controlling fermentative acidosis in the gastrointestinal tract.

A suitable agent of the first embodiment of the invention may comprise an antibiotic whose action is to control lactic acid producing gram-positive bacteria. An agent may also comprise exogenous enzyme preparations designed to reduce the passage of fermentable carbohydrate to the hind gut through improving the digestion and absorption in the intestine of starches disaccharides oligosaccharides, non-starch polysaccharides, protein starch complexes and any polysaccharide which is incompletely digested in the intestine but which is readily fermentable in the hind gut. Furthermore, an agent may comprise bentonite kaolinite, montmorrilonite or zeolite type clay preparations which reduce the rate of fermentation and bind specific ions in a way which reduces the adverse effects of rapid fermentation of starch and other soluble carbohydrates in the gastrointestinal tract The method of the First embodiment may comprise treating said animal or human with a therapeutically effective amount of an agent, wherein the agent is selected from the group consisting of a glycopeptide antibiotic, a glycolipid antibiotic, a staphylomycin antibiotic, a polypeptide antibiotic, a macrolide antibiotic, a sulphur-containing peptide antibiotic, a lincosamide antibiotic, tiamulin, a nitrofuran antibiotic, a tetracycline antibiotic, a penicillin antibiotic, a polythiazole antibiotic, an ionophore antibiotic, a cephalosporin antibiotic, a sulphonamide antibiotic, an aminoglycoside antibiotic, a quinalone antibiotic, ardacin, novobiocin sodium, bottromycin tartrate, streptogramin, nitrovin (payzone) or enramycin and other antibiotic active against gram-positive bacteria responsible for the production of acid in the gastrointestinal tract, and any combination thereof: exogenous enzyme preparations; and clays selected from bentonite, kaolinite, montmorrilonite or zeolite type clay preparations.

Typically, preferred antibiotics active against gram-positive bacteria include glycopeptide antibiotics, more typically, avoparcin or vancomycin; glycolipid antibiotics, more typically flavomycin (bambermycin): staphylomycin antibiotics, more typically virginiamycin: polypeptide antibiotics more typically bacitracin zinc, bacitracin methylene disalicylate virginiamycin S or polymixins (B & E); macrolide antibiotics, more typically tylosin, spiramycin, virginiamycin M, josamycin, spectinomycin or erythromycin or sulfur-containing peptide antibiotics, more typically thiopeptone, thiopeptin, sulfomycin, thiostrepton, sporangiomycin, siomycin or taitomycin; lincosamide antibiotics more typically lincomycin or clindamycin; or tiamulin; or nitrofuran antibiotics, more typically nitrofurantoin, nitrofurazone or furazolidone; tetracycline antibiotics more typically chlortetracycline or oxytetracycline; penicillin antibiotics more typically penicillin V or ampicillin; polythiazole antibiotics, more typically nosiheptide; or ionophore antibiotics more typically lasalocid, tetronasin, naracin or salinomycin: or ardacin novobiocin sodium, bottromycin tartrate, streptogramin nitrovin (payzone) or enramycin or any combination thereof.

Typically preferred enzymes for the break down of non-starch polysaccharides and starches include the following: glyconases including amylase, maltase, invertase, α-glucosidases, emulsin and amyloglucosidase; glucanases β-glucanase, xylanase; enzymes which break down galactosides of the raffinosse series and other α-galactosides including α-galactosidase enzymes which depolymerise non-starch polysaccharides including arabinoxylans and β-glucans and enzymes active in the break down of colloidal polysaccharides, pectic substances, which include galactouronans, galactan and arabinans, as well as the neutral polysaccharides such as xyloglucans and galactomannans and other non-starch polysaccharides Such as rhamnogalactouronan with arabinose and galactose, arabinogalactan, glucan, xyloglucan, galactouronan with arabinose and uronan with arabinose. These enzymes can be used individually or in combination.

Typically, preferred clays for reducing the rate of fermentation the osmotic effects of rapid fermentation within the glut include kaolinite bentonite, montmorrilonite or zeolite types of clay and these can be activated by a wide range of ions including sodium, calcium, potassium and mixtures of these and other ions. These clays can be used individually or in combination.

Typically the antibiotic and/or enzyme preparation and/or clay preparation can be administered by binding it to fibrous materials which pass undigested into the caecum, colon or other part of the hind gut or it can be incorporated into specially formulated feeds and foods or administered in the form of pastes gels, gums, pellets or cubes. In one particular form of the invention administration of the antibiotic to human subjects is in the form of digestible capsules which release the active material into the stomach, intestine or hindgut.

The exogenous enzyme preparations should be administered with the carbohydrate feed. Enzymes can be mixed with the feed during preparation, added to the feed before consumption or oral administration or sprinkled on top of the food before it is consumed. Enzymes can be mixed with herbs and spices coating starch based foods such as biscuits and snack foods. They can be included in pelleted feeds for animals and or in loose mixes.

Typically the enzyme preparation can be administered by incorporation into specially formulated feeds and foods or administered in the form of powders, premixes, pastes, gels, gums, pellets or cubes. In one particular form of the invention, administration of the antibiotic to human subjects is in the form of digestible capsules which release the active material into the stomach, intestine or hindgut.

According to another aspect of the invention treatment is provided for any situation whereby starch or sugars are fermented in any part or compartment of the gastrointestinal tract in a way which results in the accumulation of lactic acid or any other combination of acids which result in low pH and is responsible for the modification of adverse behaviour and for the treatment or prevention of diarrhoea, skin disorders and infections of the hind gut associated with acidic conditions.

According to another form of the invention the antibiotic and/or enzyme preparation and/or clay preparation can he used together.

According to a further embodiment of the invention, the method is for treating animals or humans which are the subject of a carbohydrate diet which is fermented to form acid in the gastrointestinal tract by controlling acid concentration during fermentative digestion in order to prevent diarrhoea and/or behavioural changes and/or skin disorders and/or infections of the hind gut associated with acidic conditions.

In a further form, the invention resides in a method of treating animals or humans which comprises delivering to the alimentary canal a quantity of an antibiotic and/or enzyme preparation and/or clay preparation of the form described above.

According to another aspect of the invention, the formulation of the antibiotic and/or enzyme preparation and/or clay preparation ensures that it is administered in a palatable form to the animal or human and in a form which retains activity and is properly mixed in the appropriate compartment(s) of the gastrointestinal tract.

Generally, the antibiotic and/or enzyme preparation and/or clay preparation is administered regularly throughout the period the animal or human is subjected to a high carbohydrate diet or to sugars or other fermentable compounds which are not efficiently absorbed prior or reaching the large intestine, colon and caecum.

More typically, the antibiotic and/or enzyme preparation and/or clay preparation is administered 1–3 times daily. Even more typically the antibiotic and/or enzyme preparation and/or clay preparation is administered once daily or can be included in human food and animal feeds. They can be fed as powders or suspended in water, included in pellets as well as being fed in premixes.

More typically the antibiotic and/or enzyme preparation and/or clay preparation is mixed with the food, or is added to feeds which contain starch or sugars which may produce an acidic pattern of fermentation in the gastrointestinal tract.

A suitable treatment may comprise the administration of a single dose or multiple doses. Usually, the treatment will consist of administering one dose daily of the antibiotic(s) for a period sufficient to control the accumulation of lactic acid by fermentation of the carbohydrate in the gastrointestinal tract. Dosing may continue while sources of carbohydrate known to cause problems of acidic fermentation in the gastrointestinal tract are included in the diet.

More typically the antibiotic and/or enzyme preparation and/or clay preparation may be administered in a single dose immediately before consuming meals containing sources of carbohydrate which are poorly digested and rapidly fermented. More typically, the antibiotic and/or enzyme preparation and/or clay preparation is administered for one day prior to and daily during the consumption of excessive quantities of food stuffs containing readily fermentable carbohydrates.

According to another embodiment of the invention, the antibiotic and/or enzyme preparation and/or clay preparation is administered orally.

The antibiotic(s) may be administered together or sequentially with an effective amount of enzyme preparation and/or clay preparation.

Compositions for administration in the method of the invention of the invention may be prepared by means known in the art for the preparation of compositions (such as in the art of veterinary and pharmaceutical compositions) including blending, grinding, homogenising, suspending dissolving, emulsifying, dispersing and where appropriate, mixing of the antibiotic and/or enzyme preparation together with selected excipients, diluents, carriers and adjuvants.

For oral administration the pharmaceutical or veterinary composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain binders acceptable in human and veterinary pharmaceutical practice, sweeteners, disintegrating agents, diluents, flavourings, coating agents preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters waxes, fatty alcohols, zein, shellac or gluten. Suitable preservatives include sodium benzoate vitamin E, alpha-tocopherol, ascorbic acid, methyl paraben, propyl paraben or Sodium bisulphite. Suitable lubricants include magnesium stearate, stearic acid, sodium oleate sodium chloride or talc. Suitable time delay agents include glyceryl monostearate or glyceryl distearate.

Liquid forms for oral administration may contain, in addition to the above agents a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols triglycerides or mixtures thereof.

Suspensions for oral administration may further comprise dispersing agents and/or suspending agents. Suitable suspending agents include sodium carboxymethycellulose, methylcellulose, hydroxypropylmethyl-cellulose, polyvinyl-pyrrolidone sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gum such as guar gum, gum acacia or gum tragacanth.

In another form the invention resides in a method of treating animals or humans which comprises delivering to the alimentary canal a quantity of an antibiotic and/or enzyme and/or clay preparation of the form described above.

The administered dose of the antibiotic can vary and will depend on several factors, such as the condition age and size of the human or animal patient, as well as the nature of the lactic acid producing gram-positive bacteria. Dosages will typically range from between 0.01 and 5 mg per kg of liveweight. More typically dosages will range from between 0.02 and 2.0 mg per kg of liveweight. More typically dosages will range from between 0.05 and 1.0 mg per kg of liveweight. Even more typically dosages will range from between 0.1 and 0.5 mg per kg of liveweight. Yet even more typically, the antibiotic is administered to the human or animal at a rate of 0.4 mg per kg of liveweight.

Typically, the antibiotic is administered at a rate of between 1 and 100 mg per kg of dry weight of food. More typically, the antibiotic is administered at a rate of between 1 and 75 mg per kg of dry weight of food. Even more typically, the antibiotic is administered at a rate of between 1 and 50 mg per kg of dry weight of food. Yet even more typically, the antibiotic is administered at a rate of between 10 and 40 mg per kg of dry weight of food.

The administered dose of the enzyme preparation can vary and will depend on several factors such as the condition, age and size of the human or animal patient, as well as the nature of the carbohydrate. Dosages will typically range from between 0.01 and 50 g/kg food (dry matter. Typically, the enzyme is administered at a rate of between 0.1 and 3 g per kg of dry weight of food. More typically, the enzyme is administered at a rate of between 1 g per kg of dry weight of food.

The administered dose of the clay preparation can vary and will depend on several factors, such as the condition age and size of the human or animal patient, as well as the nature of the carbohydrate. Dosages will typically range from between 0.5 and 100 g/kg food dry matter. Typically the clay is administered at a rate of between 1 and 50 g per kg of dry weight of food. More typically, the clay is administered at a rate of between 20 g per kg of dry weight of food.

DESCRIPTION OF THE PREFERRED EMBODIMENT

Figure 1:
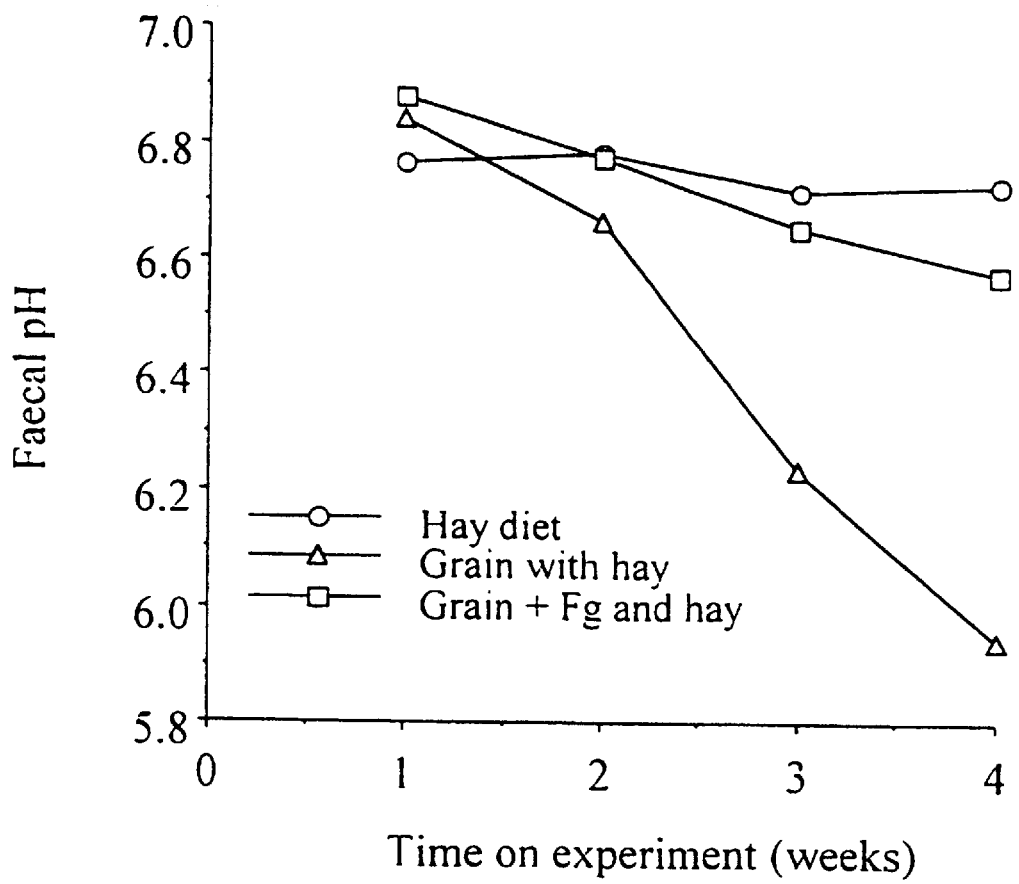
FIG. 1 shows the incidence of adverse behaviour recorded as the average total number of times each horse was seen to chew wood, eat faeces or bedding or grasp or wind suck during 14 hours of observation in a single week (2 hours observation each day). Horses were fed hay only (○), hay with increasing levels of grain (Δ) or grain with Founderguard supplying 0.05 mg virginiamycin/kg body weight/day (□). In week 1 all animals were fed hay only. In week 2 horses ted grain received 25% of the diet as grain in week 3 these horse received 50% of the diet as grain and in week 3 they were fed 75% of the diet as grain.

The main feature of the current invention is that the more subtle side effects of gut acidity resulting from starch and/or sugar fermentation were previously unknown. The present invention reveals the link between the fermentation of starch and/or sugars in the gastro intestinal tract, low pH and a range of conditions including adverse behaviour, diarrhoea, skin disorders and infections of the hind gut associated with acidic conditions.

There is significant variability between individual humans and between individual animals within any species in the efficiency and extent to which different sugars, starches, non-starch polysaccharides and other carbohydrates are digested in the acidic stomach and absorbed from the small intestine. Particularly in young animals and humans and in aging humans and animals there may be deficiencies in the gut enzymes responsible for the break down of disaccharides, starches and/or non-starch polysaccharides. There can also be deficiencies in active absorption of sugars from the intestine. These abnormalities can lead to high levels of readily fermentable carbohydrate entering the hind gut. In addition, when there is a sudden change in diet involving the introduction of starch or other fermentable carbohydrate which has not previously been in the diet or which has been in the diet at very much lower amounts, the appropriate endogenous enzymes may not be present in sufficient quantities and/or active absorption mechanisms for simple sugars may not be developed to efficiently digest and absorb all readily fermentable carbohydrate. This may also lead to high levels of fermentable carbohydrate entering the hind gut. There can therefore be considerable variation between individuals in the nature and in the amount of fermentable substrate reaching the hind gut. It is known that some humans, and particularly children, develop adverse behaviour patterns following consumption of particular foods such as those containing sugars and or processed starch. It is also known that animals such as horses develop adverse behaviour such as eating their bedding, coprophagy, chewing wood, and being highly excitable when they consume high levels of cereal grain containing starch. Piglets and other animals may develop behavioural problems of chewing tails and "boredom" when they are fed diets based on cereal grain for rapid growth rate and production. Poultry can also develop adverse behavioural patterns such as vent pecking and cannibalism when on high grain diets.

Diarrhoea can be a major problem for all species as it leads to the loss of minerals and electrolytes. It is also a condition which is inconvenient and embarrassing for humans and/or for dogs which are kept indoors. The reason for chronic diarrhoea is often unknown in many situations where clinical disease conditions are not diagnosed.

Horses on high levels of grain or grazing lush green pasture are given daily doses of virginiamycin, or any other antibiotic compound with a similar or better effect on fermentation and digestion, formulated to reach and mix with the contents of the caecum in order to stop the animal from chewing the wooden rails of the stables and/or those surrounding the paddock and to make the animal easier to handle and more pleasant to ride.

Piglets are fed diets including virginiamycin, and/or any other antibiotic compound with or without clay and enzyme preparations in order reduce the incidence of tail biting.

Cattle entering a feedlot and given high levels of grain are fed the concentrate part of the diet containing virginiamycin, or any other antibiotic compound with a similar or better effect on fermentation and digestion, to improve their feeding behaviour and reduce signs of stress and reduce diarrhoea.

Children displaying hyperactivity and/or attention deficit disorder and/or another conditions or behavioural trait related to intake of a particular sugar, starch or other dietary ingredient containing fermentable carbohydrate are even thiopeptin, or any other antibiotic compound with a similar or better effect on fermentation and digestion, to control fermentation and digestion and restore normal behaviour.

Compounds Such as exogenous enzyme preparations may be consumed with particular foods in order to assist their digestion prior to hind gut fermentation and acid formation. The use of antibiotic feed additives can also be included in order to provide further protection against acidic fermentation in the hind gut in conjunction with food and drinks specially prepared for children with particular problems associated with hyperactivity or other behavioural problems associated with the intake of readily fermentable carbohydrates.

There are numerous recorded examples of skin conditions such as psoriasis which respond to changes in the amount and type of carbohydrate consumed. The fermentation and the subsequent acid build up which leads to these conditions are unknown subtle effects of sub-clinical hind gut acidosis. Treatment of these conditions involves the administration of an effective antibiotic compound, such as virginiamycin, active against the gram positive bacteria which produce such acid. Antibiotic treatment to control acidic fermentation can be used on its own or in conjunction with exogenous enzyme preparations. Enzyme preparations may be effective on their own when used with specific feeds or in situations where specific digestive and absorptive deficiencies are known.

Infections of the hind gut such as wine dysentry can be controlled by preventing acidic conditions in the gut as a result of rapid fermentation of dietary carbohydrates. The use of enzymes to increase the efficiency and extent of starch and other carbohydrate digestion prior to the hind gut may be used as an alternative or an adjunct to the use of antibiotics and/or changing the form of carbohydrate portion of the diet in order to control these hind gut pathogens.

The invention will now be described in greater detail by reference to specific Examples.

EXAMPLE 1

Experiment 1 (Murd D94)

The horse was chosen as the primary example for the demonstration of the behavioural ap sects of this invention. The horse has a digestive system similar to many monogastric omnivores such as man, pigs, dogs, poultry etc. It has a hind out which is larger, in proportion to body size, than these other species.

Eighteen mature Standardbred horses were selected on the basis that they showed no signs of lameness and that they had no obvious unusual behavioral characteristics. They were assigned at random to one of three treatment groups (6 per treatment) summarised in Table 1.

TABLE 1

Feed intake (kg/d) of horses fed hay alone, or hay with increasing levels of grain-based pellet with or without the addition of virginiamycin (as Founderguard)

| Treatment group | Week 1 | Week 2 | | Week 3 | | Week 4 | |
| --- | --- | --- | --- | --- | --- | --- | --- |
| | Hay | Hay | Grain | Hay | Grain | Hay | Grain |
| Hay only | 8 | 8 | | 8 | | 8 | |
| Hay and grain | 8 | 6 | 2 | 4 | 4 | 2 | 6 |
| Hay and grain with Founderguard | 8 | 6 | 2 | 4 | 4 | 2 | 6 |

*Founderguard contains virginiamycin at a rate of 1% and was administered to provide 5 g Founderguard/100 kg liveweight.

The "grain" portion of the diet consisted of a pellet containing: Wheat (72%); Soybean (15%); Lupin (10%) and Minerals/vitamins (3%). The hay was fed in the long form (not chaffed). All animals ate all of the feed offered in two equal feeds in the morning and afternoon.

For the week before the experiment started, all of the horses were observed daily when grazing as a single group to determine if there were any abnormal (background)

behavioural patterns. The horses were then brought into a stable complex with a high overhead walk way from which all of the animals could be observed without being disturbed. Behaviour was observed and quantified during a 1 hour session each morning before feeding and a 1 hour session each evening after feeding. Every aspect of behaviour was accurately defined before the experiment started and each incident of every type of behaviour was recorded during the periods of observation.

In addition to the observations while the animals were in their stalls they were exercised each day and examined for any signs of lameness. Samples of faecal material were taken for analysis or pH. Blood samples were also taken for measuring pH, blood gas concentrations and lactic acid. The animals were weighed each day. At the end of the experiment all animals were humanely slaughtered in order to take samples of the digestive tract. During this process the digestive tract was weighed.

Figure 2:
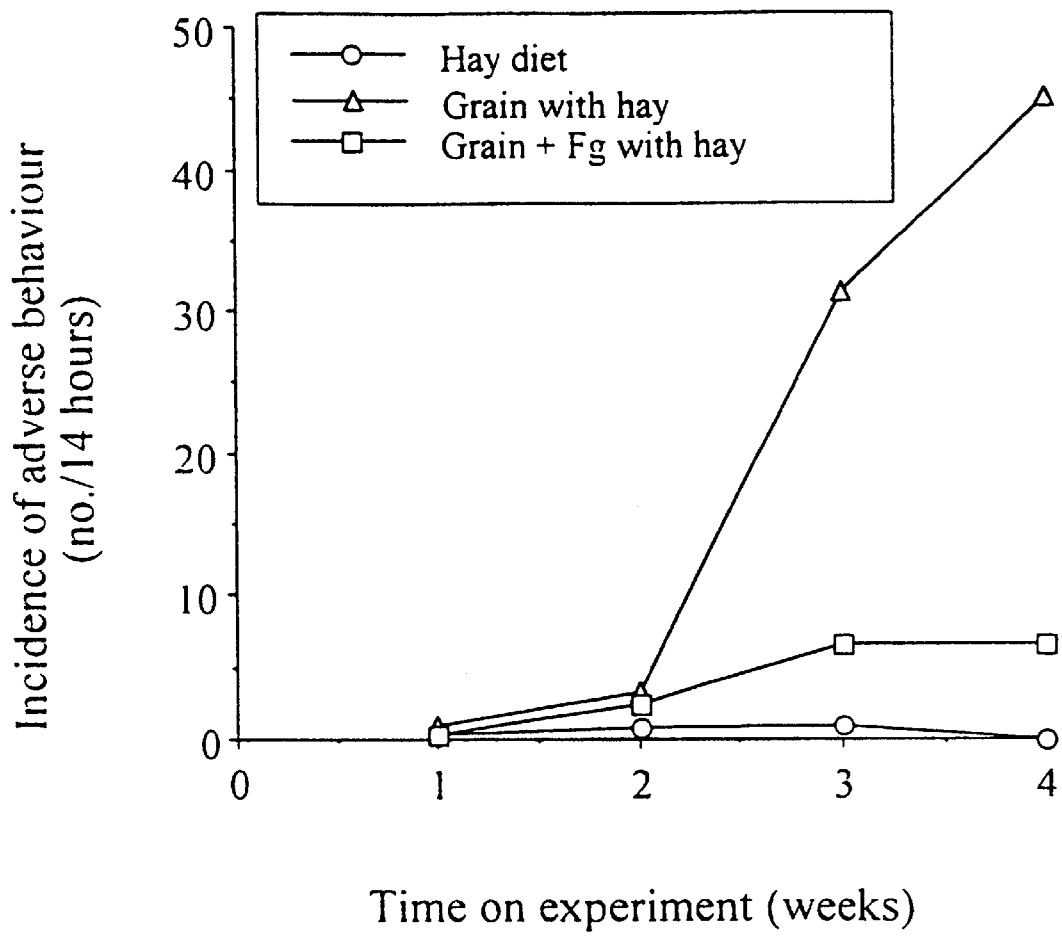
FIG. 2 shows the changes in faecal pH in horses fed hay only (○), hay with increasing levels of grain (Δ) or grain with Founderguard supplying 0.05 mg virginiamycin/kg body weight/day (□). In week 1 all animals were fed hay only. In week 2 horses fed grain received 25% of the diet as grain, in week 3 these horse received 50% of the diet as grain and in week 3 they were fed 75% of the diet as grain.
Figure 3:
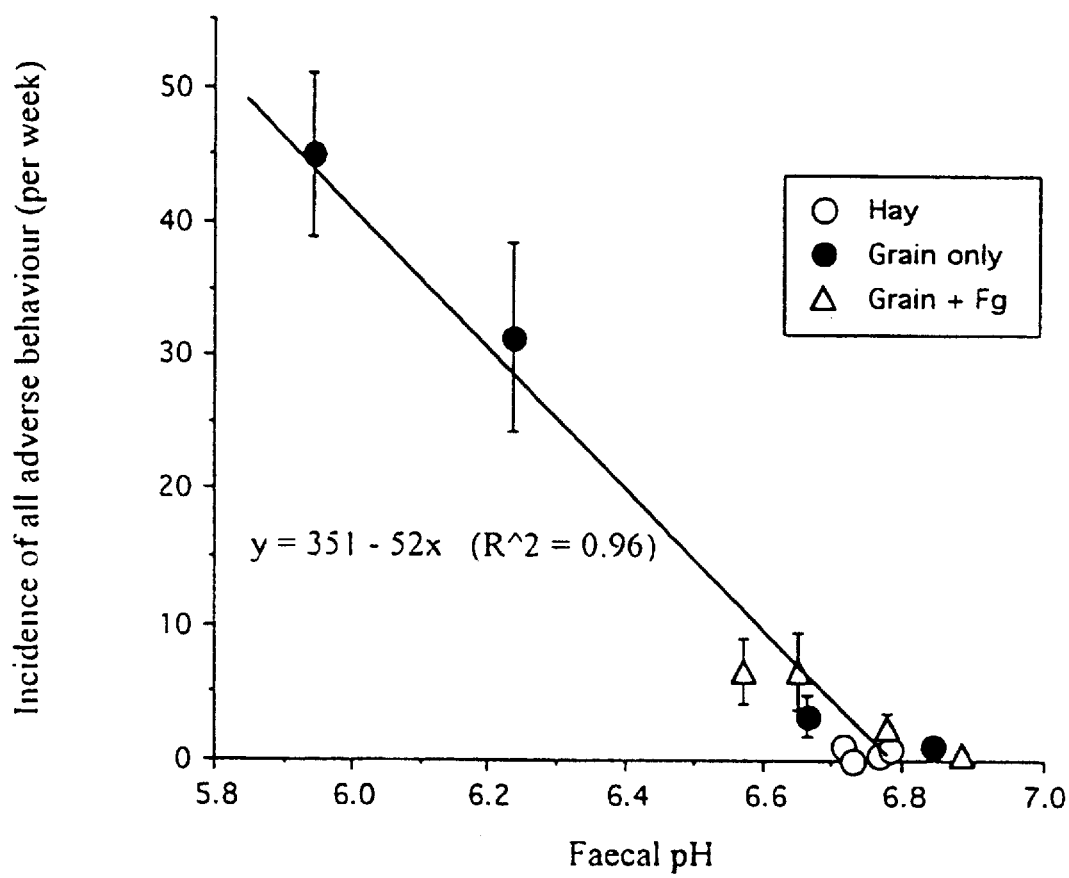
FIG. 3 shows the relationship between the sum of all incidence of adverse behaviour (wood chewing, eating bedding and grasping) per week and the average faecal pH during the corresponding week.

There were marked changes in the behaviour of horses fed increasing levels of grain without Founderguard (FIG. 1). During the same time the behaviour of the horses maintained on hay only remained normal indicating that the development of abnormal behaviour was a result of change in diet rather than boredom at being housed in a stable. The behaviour of horses fed grain with Founderguard was marginally, but not significantly different from those fed hay. In animals fed grain without Founderguard there was a significant decreased in faecal pH with increasing levels of grain in the diet. The faecal pH of horses fed grain with Founderguard was similar to those fed hay (FIG. 2). The incidence of adverse behaviour was closely related to faecal pH ($R^2$=0.96) (see FIG. 3). With more acidic conditions in the hind gut as indicated by reduced faecal pH, there was a far greater incidence of adverse behaviour.

When the horses were weighed each day they were also observed in the yards. All horses seen to be rearing and or kicking during the last week of feeding were identified as being in the group fed grain only. None of the animals fed grain with virginiamycin or hay on it's own were observed to have this type of behaviour.

Although the animals fed grain consumed higher levels of digestible energy there was an average weight loss of around 7 kg compared to the horses fed only hay. This difference in liveweight was not statistically significant but the corresponding reduction in the weight of the gut of around 20 kg, in horses fed increasing levels of grain relative to hay, was highly significant. Table 2 shows that it was not an empty gut feeling that caused hunger and/or boredom which initiated the abnormal behavioural patterns since both groups of horses which were fed grain had similar changes in the gut weight.

TABLE 2

Summary of changes in liveweight of horses during the final 3 weeks of the experimental period and the weight of the gastrointestinal tract at the end of the experiment.

|  | Hay | Grain only | Grain + Fg* | Signif (P) |
|---|---|---|---|---|
| Average weight change (kg/21 d) | 0.7 | −7.0 | −7.5 | 0.2 |
| Weight of gut (kg) | 86 | 63 | 68 | 0.0002 |
| Weight of gut as % of live weight | 18 | 13 | 15 | 0.0001 |

*Fg = Founderguard contains virginiamycin at a rate of 1% and was administered to provide 5 g Founderguard/100 kg liveweight.

Many of the effects of feeding grain to horses are complicated by the fact that there is normally an increase in the amount of digestible energy intake, a reduction in the amount of bulk consumed and a different pattern of fermentation and digestion within the cut. The use of virginiamycin (as Founderguard) allows us to demonstrate the effects of acid build up in the gut without any confounding factors such as the amount of energy available or the physical nature of the diet when changing from long fibrous roughage to grains or pelleted feed. The results of these studies therefore indicate that the adverse effects of behaviour changes, associated with feeding cereal grain were a direct effect of increased gut acidity due to fermentative digestion and that this problem can be overcome by controlling the build up of acidity in the hind gut. In this study the control of acidity was achieved using virginiamycin. Similar effects can be expected with the use of appropriate exogenous enzyme preparations to enhance starch and sugar digestion and thereby reduce hind gut fermentation and the build up of acidity. The use of a combination of enzymes and antibiotic would also be efficacious.

EXAMPLE 2

Experiment 2 (GMS, Brisb M95)

A Thoroughbred gelding being fed grain supplements in preparation for a show riding event developed behavioural characteristics which made it very hard to handle and ride. Before riding the horse it was necessary to lunge the animal for approximately 30 minutes to overcome its urge to buck the rider off. Following administration of virginiamycin in the form of Founderguard for 1 week it was then possible to ride the horse without any of the adverse behavioural effect such as bucking. The rider reported the horse to be more manageable and far easier to handle.

Experiments 1 and 2 show that behavioural changes associated with high grain diets in horses can be prevented or reversed through using virginiamycin as Founderguard to control gut acidosis. This link between the use of virginiamycin and behavioural changes is completely novel.

EXAMPLE 3

Experiment 3 (NE M95)

Experiment 3 provides an example of how a number of riders have identified significant changes in the behaviour of horses following treatment with virginiamycin.

Two paddocks were leased for the experiment on a property in the Black Mountain area between Armidale and Guyra, NSW, Australia. The rainfall in this area is normally reliable and this factor together with the high altitude 1250 m and the rich basaltic soils were considered to provide a good combination of conditions for the production of pasture with high levels of soluble carbohydrate. Conditions for high carbohydrate levels characterised by warm clear days, which facilitate rapid photosynthesis during the day, followed by cold nights. The low night temperatures slow down the process of respiration and retard the break down of carbohydrates. Good soil moisture and soil fertility are also important to achieve rapid growth and optimal photosynthetic activity.

One paddock was approximately 25 ha and the other around 12 ha. Twenty five mature female ponies were selected for the experiment and were identified with numbered tags secured around the neck with a strap and buckle.

20 ponies were selected on the basis of uniform size and signs of fatness (rib cover and cresting of the neck). Ten of these animals were given Founderguard (1% virginiamycin)

at the rate of 5 g/100 kg live weight by feeding them individually in a race. At the same time a rectal sample of faecal material was taken from each animal for assessment of consistency and for measurement of pH. Subsamples were taken for analysis of dry matter, lactic acid and volatile fatty acid concentrations. These subsamples were placed in plastic bags in ice for transport to the laboratory and were then kept at −20° C. prior to analysis. Samples of pasture were taken by plucking grass and clover plants in a way which was designed to simulate grazing selection. These samples were also transported back to the laboratory in plastic bags in ice and then stored at −20° C. prior to drying (55° C.) for analysis of dry matter and soluble carbohydrate content.

This experimental period of daily treatment with Founderguard and faecal and pasture sampling was continued for a further week.

Figure 4:
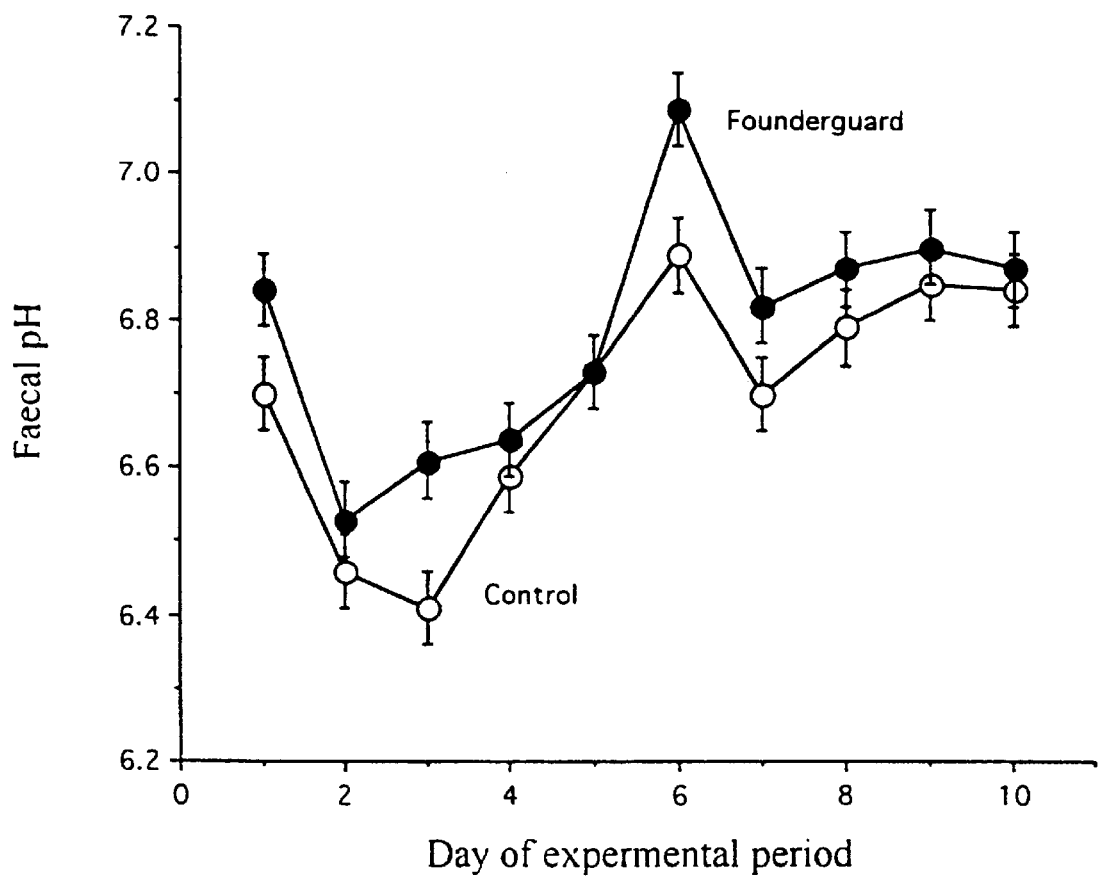
FIG. 4 shows the chance in faecal pH with time in horses with no treatment or given Founderguard each day.
Figure 5:
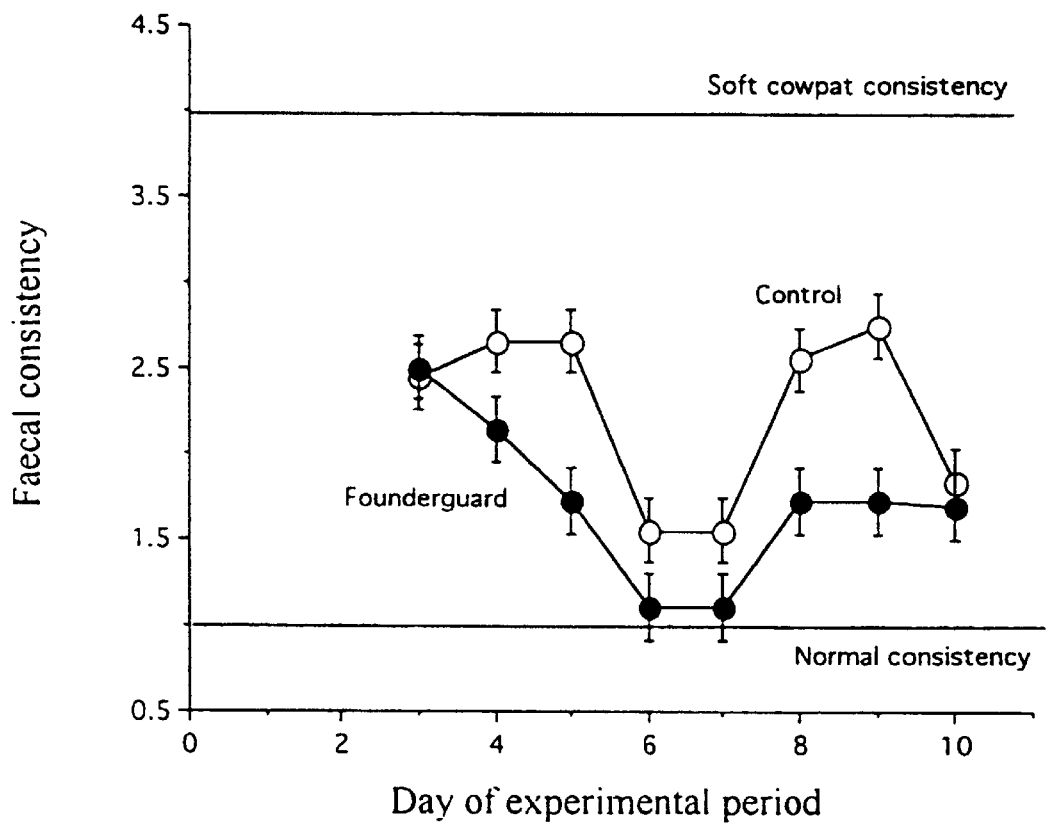
FIG. 5 shows changes in the consistency of faecal material with time in horses with no treatment or given Founderguard each day. The consistency of faecal material was assessed using the following scale: 1. Firm well formed balls 2. Soft but still in well formed balls 3. Ball formation not pronounced 4. No form and of a soft consistency 5. Soft semi-fluid material.

There was a significant (p<0.001) effect on faecal pH (FIG. 4) and faecal consistency (FIG. 5) as a result of treatment with Founderguard. Founderguard increased faecal pH by an average of 0.1 pH unit which is equivalent to a difference between treatments of 25% in the concentration of $H^+$ ions in faecal material. The difference between treatment groups in the acidity of the faecal material was explained by differences in the concentrations of both lactic and volatile fatty acids (VFA). The concentrations of lactic acid, VFA and the proportions of the different acids are summarised in Table 3. There was twice the concentration of VFA in the faecal material of horses without Founderguard (p<0.001). Although there was around three times as much lactic acid in horses without Founderguard this difference was not significantly different due to the considerable variation between horses in the concentration of lactic acid. There was a significant correlation between faecal pH and faecal consistency (p<0.01) $R^2$=0.151.

TABLE 3

Dry matter content, pH and concentrations of volatile fatty acids (VFA) and lactate in faecal samples taken on day 3 of the trial.

|  | Control | | Founderguard | | Sign |
| --- | --- | --- | --- | --- | --- |
|  | Mean | se | Mean | se | P |
| Dry matter (%) | 16.6 | 0.6 | 17.1 | 0.9 | ns |
| Lactate mmol/g DM | 18 | 9.7 | 5 | 3.0 | ns |
| VFA mmol/g DM | 551 | 37.0 | 257 | 25.6 | *** |
| Total acid | 569 | 42.6 | 262 | 26.6 | *** |
| % Acetate | 78 | 0.9 | 75 | 2.3 | ns |
| % Propionate | 11 | 1.2 | 15 | 1.5 | ns |
| % Butyrate | 5 | 0.3 | 5 | 0.6 | ns |
| pH (day 3) | 6.41 | 0.015 | 6.61 | 0.015 | * |

The results show that even under conditions which would be considered normal the faecal pH can be lower than ideal and faecal consistency is related to reduced faecal pH. It is very interesting that under these conditions Founderguard still has a highly significant effect on faecal pH through reducing the concentrations of acids. Soluble carbohydrate and starch entering the hind gut will be rapidly fermented to produce of VFA and lactic acid. The accumulation of acids in the gut in turn increase the rate of flow of digesta and this brings more undigested carbohydrate into the hind gut for fermentation. This cycle is likely to cause chronic acidosis of the hind gut and a pattern of digestion which could be dangerous under conditions of rapidly rising levels of soluble carbohydrate in the diet. In this experiment the levels of soluble carbohydrate in both grasses and clover increased by around threefold in the space of 1 or 2 days and reached concentrations of around 30% of dry matter. This sudden change in the composition of pasture species is similar to a sudden increase in the amount of starch fed as cereal grain. In horses consuming around 10 kg of pasture dry matter per day 30% of soluble carbohydrate represents 3 kg of sugars which is equivalent to around 4 kg of barley or wheat. While it is likely that a lot of sugars are digested and absorbed prior to reaching the hind gut there is almost certainly incomplete digestion in the small intestine due to rapid passage of digesta during the intake of large quantities of fresh plant material. There is also likely to be limited capacity of enzyme systems for handling sugars in the small intestine when the dietary conditions change suddenly.

The effect of Founderguard on faecal pH and the concentration of acids in faecal material is a very interesting and important finding. It is possible that part of the effect of Founderguard is to reduce the overall extent of fermentation and digestion but this has not been shown to be significant in monogastric or ruminant animals. The major effect of Founderguard is more likely to be due to the specific action of virginiamycin in controlling proliferation of the gram positive lactic acid producing organisms in the hind gut. Exogenous enzyme preparations may assist by improving digestion of carbohydrate in the small intestine and reduce the extent of acidic fermentation in the hind gut. In this way antibiotics and enzymes may be used independently or together.

EXAMPLE 4

Experiment 4 (Mur F95)

The aim of this study was to investigate behavioural changes in race horses on high grain diets with or without Founderguard. This experiment introduces the link between faecal consistency, low pH and the control of both of these conditions with virginiamycin to prevent acid accumulation.

Sixteen trainers in the Perth district agreed to select one horse from their stables for the trial. Selection was on the basis of the horse being fed high levels of grain and considered to have some behavioural problems such as being difficult to handle, excitable and unpredictable.

A placebo batch of Founderguard was manufactured which was indistinguishable from the medicated product. The placebo and medicated product (1% virginiamycin) were packed into identical buckets and were labelled either with letters or numbered in a random way. The labelling code was not known by the person organising the trial who was provided with 16 pairs of buckets, each pair included placebo and active product. Each trainer was given one bucket for a two week period and then the second bucket for a further two week period. Neither the trainer nor the person organising the trial had any knowledge of which bucket contained the active Founderguard (1% virginiamycin).

Trainers were asked to record any incident of tying up or any other abnormal development in the health and welfare of the animals involved in the trial.

The behaviour of each horse was assessed prior to the start of the trial and at least once during each two week period by both trainer and the veterinarian conducting the trial. In addition the trainers, riders and strappers were asked if they observed any change in behaviour or any adverse effects when the horses were on either of the treatments.

There were no veterinary problems or incidents of tying up recorded during the trial period in any of the horses.

There was a very wide range in the behavioural idiosyncrasies of individual horses. The best measure was the overall opinion of trainers, veterinarian, riders and strappers as to whether behaviour had improved, got worse, or there was no change when Founderguard was given, compared to when the placebo was administered. In cases where there was a range of opinions as to whether any change had taken place this was recorded as no chance. There was always better agreement and more uniformity in rankings involving improved behaviour than there was in assessments involving worse behaviour.

| Response to Founderguard | Number of Horses |
| --- | --- |
| No Change | 5 |
| Worse | 2 |
| Improved | 9 |

The data were analysed using a paired t-test by assigning values of 0 for no change −1 worse and 1 for improved and were compared against 0 as the control behaviour on placebo. This analysis indicates a significant (p=0.029) improvement in behaviour and handling as a result of using Founderguard.

The effect of Founderguard on behaviour is consistent with the observations of several prominent hack riders who have tried Founderguard during the preparation of horses for competition.

EXAMPLE 5

Experiment 5 (JBR M95)

Experiment 5 and 6 demonstrate the efficacy of virginiamycin in controlling diarrhoea in the dog.

A golden retriever dog (approx 43 kg) with a long history of sporadic diarrhoea was used in an experiment over a period of 12 months. Throughout the experimental period the dog was treated with ivermectin in the form of monthly chewable tablets (Merck Sharp and Dohme) against heart worm. Several dietary regimes and the use of virginiamycin were investigated as a means of controlling hind gut fermentation and the development of acidic conditions in the caecum and colon.

Pelleted or extruded dog food contains significant levels of cereal grain and starch, mainly in the form of wheat. Tinned wet dog food also contains cereal grain. The dog was fed a diet based on either extruded pellets or a mixture of pellets and tinned food for a period of around 18 months prior to the start of the experimental period and faeces during this time were continually soft and unformed with occasional episodes of severe diarrhoea. An investigation of parasitic infection during an episode of diarrhoea indicated nil infection and this was ruled out as a cause of the diarrhoea. No veterinary explanation was available as to the cause of the soft unformed faeces and the episodes of diarrhoea.

During the experimental period the diet was changed in a number of ways and treatment with virginiamycin was investigated as a means of controlling the diarrhoea through its effect on fermentation and hind gut acid concentration. The dietary regimes tested and the results are summarised in Table 4.

TABLE 4

Dietary treatments
and their effect on faecal consistency in a golden retriever dog

| | |
| --- | --- |
| Boiled rice | Faeces normally well formed. Several incidents of mild diarrhoea. |
| Boiled rice and virginiamycin | Faeces well formed and normal. No diarrhoea. |
| Pelleted dog food | Faeces nearly always soft and unformed. Numerous episodes of severe diarrhoea. |
| Pelleted dog food with virginiamycin | Faeces normally well formed and very rare incidents of mild diarrhoea. Severe diarrhoea when virginiamycin accidentally excluded even for short periods. |
| Tinned dog food | Faeces normally soft. Only occasional episodes of mild diarrhoea. |
| Tinned dog food with virginiamycin | Faeces well formed and normal. No diarrhoea. |
| Boiled rice tinned dog food | Faeces normally well formed and normal. Occasional soft faeces and isolated incidents of mild diarrhoea. |
| Boiled rice and tinned dog food with virginiamycin | Faeces well formed and normal. No diarrhoea. |

The dog food were commercial products. The tinned dog food was 'Chum' and the pelleted/extruded dry feed was 'Pal'. Both products were supplied by Uncle Ben's of Australia (Kelly Street Wadonga, Victoria 3690 Australia). Each treatment was given until there was a clear change in faecal consistency. The treatments were repeated in a randomised design throughout the year. The results are summarised above.

EXAMPLE 6

Experiment 6 (JBR J95)

Virginiamycin was given to a commercial kennel where there was a history of some dogs developing diarrhoea when they first arrived. A number of dogs were treated with virginiamycin at a dose rate of approximately 0.4 mg/kg liveweight per day when they developed diarrhoea on arrival at the kennel. These animals all returned to passing normal faeces within 48 hours after first treatment and treatment was stopped after three days.

EXAMPLE 7

Experiment 7 (Mur F95)

Experiment 7 provides further evidence that starch passing undigested to the hind gut is the principle cause of the build up of acid and diarrhoea.

Piglets were fed diets based on either boiled rice or wheat with a protein supplement based on meat meal. All animals were fed the experimental diets for 4 weeks before being slaughtered at 8 weeks of age. Samples of digesta were analysed for pH, dry matter and the concentrations of volatile fatty acids. The dry matter content and the pH of the faeces was significantly higher in the case of pigs fed diets based on boiled rice than those fed wheat-based diets. In this study, the piglets were also challenged with an articial infection of *Serpulina hyodysenteriae* oral administration of the bacteria which produces swine dysentry.

Figure 6:
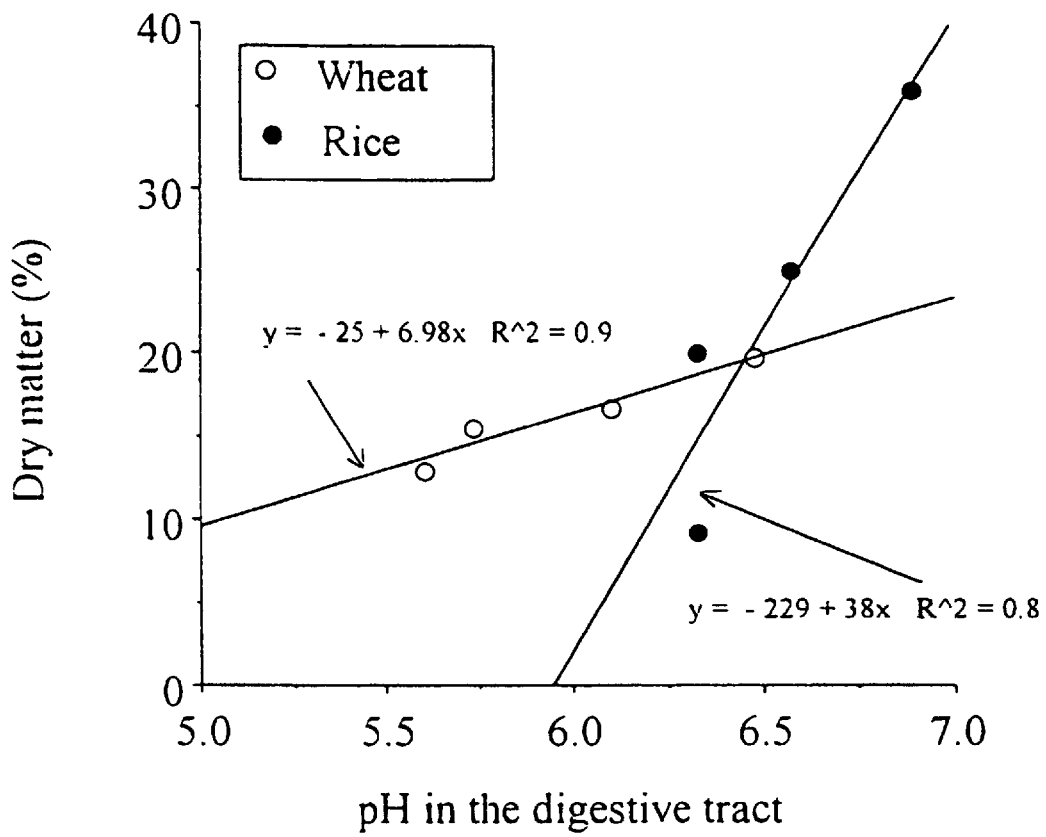
FIG. 6 shows the relationship between the pH and dry matter content of digesta in different parts of the digestive tract of pigs fed diets based either on based rice or wheat. The highest pH and dry matter is for faecal material and the lowest pH is caecal digesta. Intermediate values are from the proximal and distal colon.

The results are summarised in FIG. 6. These show that there is a very good relationship between acidity in the gut (pH) and the dry matter content of the digesta. This relationship changes between diets but within each diet variation in pH explains between 80 and 90% of the variation in dry matter content. The results also indicate that the difference between diets in the faecal dry matter content can largely be explained by the acidity of the digesta.

The average concentration of volatile fatty acids in the colon of pigs fed wheat was 32.9 mmol/L compared to 12.7 mmol/L in those fed boiled rice. This is one of the major reasons for the difference in pH and dry matter content of digesta and faecal material between the two diets.

The change in the source of carbohydrate from wheat to boiled rice prevented the establishment of swine dysentry disease.

One of the main differences between wheat and rice is in the non-starch polysaccharides. Wheat has much higher levels of non-starch polysaccharides than rice and this reduces the amount of carbohydrate digested and absorbed in the intestines. There is therefore more fermentation of carbohydrate in the large intestines (hind gut) and this leads to more accumulation of acids lower pH and lower dry matter content. The use of enzymes to overcome the adverse effects on starch digestion associated with cereal based diets such as wheat, barley and rye, prevents the development of acidic conditions in the hind gut and provides a new way of preventing hind gut diseases such as swine dysentry where the pathogens rely on an acidic environment to establish a competive advantage.

EXAMPLE 8

Experiment 8 (MEX:JBR)

Experiment 8 provides evidence of the effect of a sudden chance in the source of dietary starch in the human diet on the incidence of diarrhoea. It is common for visitors to Mexico to develop diarrhoea shortly after arrival from other countries. It is generally believed that this is a result of poor hygiene.

Two volunteers, one male and one female around 25 years of age and in perfect health entered Mexico to visit Merida (Yucatan) on three separate occasions over period of 18 months from the Dominican Republic where they were semi-permanent residents. Each visit lasted between 10 and 16 days. Both the Dominican Republic and Mexico are tropical countries and there is a similar standard of hygiene and standard of living. During each visit the subjects meticulously maintained similar standards of hygiene. When they were not directly responsible for food preparation themselves they ensured that standards of hygiene were in food preparation were to their normal standards.

On each visit to Mexico both subjects developed chronic diarrhoea for a period of at least one week after which time faecal consistency slowly returned to normal. The major difference in the diet of the subjects was in the source and amount of carbohydrate consumed. In the Dominican Republic the main source of dietary carbohydrate was wheat (bread) and root vegetables such as cassava and sweet potato. In Mexico the main source of carbohydrate was maize (tacos, tortillas etc). In addition, carbohydrate made up a far greater proportion of the diet in Mexico than it did in the Dominican Republic.

It was concluded that the change to high levels of maize in the diet resulted in fermentable carbohydrate passing to the hindgut and that the diarrhoea was of an osmotic nature, from high levels of acid in the hind gut, rather than secretory diarrhoea from the establishment of pathogenic bacteria in the intestine. It is likely that this form of diarrhoea, resulting from excessive hind gut fermentation, can be controlled by antibiotic feed additives such as virginiamycin. Exogenous enzyme preparations may also be effective in increasing the digestion of maize starch until the endogenous systems adapt. Again antibiotic additives or enzymes can be used independently or together.

EXAMPLE 9

Experiment 9 (Alm.Roc)

The presence of β-glucans in cereal grain are known to be responsible for lower nutritive value of grains such as barley. The use of exogenous β-glucanase enzyme is described in this experiment to improve the digestion and absorption of starch before it reaches the hind gut in broiler chickens.

Broiler chickens were fed diets based on maize or barley grain to supply 60% of the feed consumed. Half of the chickens on each basal diet were given β-glucanase enzyme at a rate of 0.129 g enzyme premix per kg of diet dry matter. This was administered by mixing the enzyme into the diet. Weight gain in chicks fed barley diets without β-glucanase enzyme were lower than those fed maize or barley with β-glucanase enzyme. The inclusion of β-glucanase enzyme in the barley diets significantly (p<0.001) improved the digestibility and absorption of starch (Table 5).

TABLE 5

Pre-ileal digestion of starch (%) in broiler chicks fed diets based on maize or barley grain with or without the inclusion of β-glucanase enzyme at 0 or 0.129 g/kg dry feed (From: M. Almirall, J. Brufau, E. Esteve-Garcia (1993) In: Enzymes in Animal Nutrition (Institut fur Nutztierwissenschaften, Zurich)

| Grain type | β-glucanase enzyme | Pre-ileal starch digestion |
|---|---|---|
| Maize | 0 | 96 |
| Maize | 0.129 | 94 |
| Barley | 0 | 89 |
| Barley | 0.129 | 96 |

EXAMPLE 10

Experiment 10 (Milt.Cyp)

Bentonite, kaolinite, zeolite and other types of clays are able to bind ions reversible and can have a significant effect on pH during fermentation in the gastrointestinal tract. The ability of these clays to absorb ions means that their inclusion in a diet can reduce the osmolarity in the gastrointestinal tract.

An experiment was conducted involving the inclusion of bentonite clay in the diets of lambs from weaning at 17.5 kg to slaughter at 37 kg. The basal diet consisted of 78% barley, 16% soybean 5% wheat bran and 1% minerals and vitamins. Bentonite was given at a rate of 20kg/tonne of feed, replacing barley, and was administered by mixing with the diet. There was a consistently higher rumen pH in lambs given the diet containing bentonite. The results are summarised in Table 6. Similar results are achieved with clays such as kaolinite and zeolites.

TABLE 6

Rumen pH and ammonia concentrations of lambs given diets based on barley with or without bentonite at a concentration of 2 kg/tonne of feed. (From S. Economides, E. Georghiades and M. Hadjipanayiotou (1987). Effects of bentonite feeding on the pre- and post-weaning performance of chios ewes and lambs ARI, Cyprus)

| Parameter | Without bentonite | With bentonite |
| --- | --- | --- |
| Rumen pH | 5.97 | 5.72 |
| Rumen ammonia (mg/L) | 97 | 122 |

The extrapolation of these findings to other species is logical since the same pattern of digestion and fermentation occurs in practically all animals including humans. There are parts of the digestive tract which are designed to support neutral pH and fermentation and there are other compartments which are designed for acid digestion. All species have the capacity for fermentation either prior to the acidic digestion or following acidic digestion and intestinal absorption. The invention therefore extends to any animal, including humans, where the fermentation of starch or sugar occurs in the gastro intestinal tract. In humans, pigs and horses, this fermentation occurs in the hind gut (caecum and colon).

Industrial Applicability

The present invention makes use of a method for the treatment or prophylaxis of adverse behaviour, diarrhoea, a skin disorder or an infection of the hind gut resulting from the accumulation of acid in the gastrointestinal tract of a human or an animal, said accumulation resulting from the fermentation of carbohydrate in the gastrointestinal tract of said human or animal, which method comprises administering to said human or animal an effective amount of an agent capable of preventing or controlling fermentative acidosis in the gastrointestinal tract.

I claim:

1. A method for the treatment or prophylaxis of adverse behavior in an animal or human resulting from the accumulation of lactic acid in the hind gut or large intestines respectively, of the gastrointestinal tract of said animal or human, wherein said lactic acid results from the fermentation acidosis of carbohydrates in the gastrointestinal tract of said animal or human, which method comprises administering to said animal or human an amount of virginamycin antibiotic that is effective to act on lactic acid producing bacteria in the gastrointestinal tract of said animal or human to control fermentative acidosis of carbohydrates in the gastrointestinal tract of said animal or human.

2. The method of claim 1 wherein said virginiamycin is administered together with a clay preparation which reduces the rate of fermentation and binds specific ions in a way which reduced the adverse effects of rapid of starch and other soluble carbohydrates in the gastrointestinal tract, or a mixture of two or more thereof.

3. The method of claim 1 wherein said virginiamycin is further admixed with at least one exogenous enzyme that reduces the passage of fermentable carbohydrates to the hind gut.

4. The method of claim 3 wherein the enzyme is selected from the group consisting of at least one of glyconases; enzymes that break down galactosides; enzymes that depolymerise non-starch polysaccharides; enzymes active in the break down of colloidal polysaccharides, neutral polysaccharides and other non-starch polysaccharides; and enzymes specific for oligosaccharides and disaccharides.

5. The method of claim 1 wherein said animal is a horse and wherein the adverse behavior is rearing, kicking, excitability, unpredictability, coprophagy, wind sucking, wood chewing and grasping, vent pecking, cannibalism or tail biting.

6. The method of claim 1 wherein said animal is human and wherein the adverse behavior is a behavioral problem associated with the intake of readily fermentable carbohydrates.

7. The method of claim 1 wherein the agent is administered during the period that the animal of human is ingesting a diet comprising sufficiently large proportions of fermentable compounds, selected from carbohydrates and sugars that are not otherwise absorbed prior to reaching the large intestine, colon and caecum, causes said adverse behavior.

8. The method of claim 7 wherein the agent is administered daily.

9. The method of claim 1 wherein the agent is administered in a single dose prior to the consumption of said carbohydrates.

10. The method of claim 3 wherein the antibiotic is administered at a rate of between 0.01 and 5 mg per kg of liveweight.

11. The method according to claim 3 wherein the antibiotic is administered at a rate of between 1 and 50 mg per kg of dry weight of food.

12. The method according to claim 4 wherein the enzyme preparation is administered at a rate of between 0.01 and 50 g per kg of dry weight of food.

13. The method of claim 1 wherein the agent is administered orally.

14. The method of claim 1 wherein the agent is delivered to the alimentary canal of the human or animal undergoing said treatment or prophylaxis.

15. The method of claim 1 wherein the agent is administered bound to fibrous materials that pass undigested into the caecum or colon.

16. The method according to claim 15 wherein the agent is incorporated into specially formulated feeds and foods.

17. The method according to claim 15 wherein the agent is administered in the form of at least one of gums, pastes, pellets or cubes.

18. The method of claim 1 wherein the administration of said agent is in the form of digestible capsules that release the active material into the stomach.

19. The method of claim 4 wherein said glyconase is at least one member selected from the group consisting of amylase, maltase, invertase, α-glucosides, emulsin and amyloglucosidase.

20. The method of claim 4 wherein said enzyme that depolymerizes non-starch polysaccharides is at least one member selected from the group consisting of arabinoxylans and β-glucans.

21. The method of claim 4 wherein said enzyme that breaks down colloidal polysaccharides is at least one member selected from the group consisting of galactouronans, galactan and arabinans.

22. The method of claim 4 wherein said enzyme that breaks down neutral polysaccharides is at least one member selected from the group consisting of xyloglucans and galactomannans.

23. The method of claim 4 wherein said enzyme that breaks down non-starch polysaccharides is at least one member selected from the group consisting of rhamnogalactouronan with arabinose and galactose; arabinogalactan; glucan; xyloglucan; galactouronan with arabinose; and uronan with arabinose.

* * * * *